United States Patent [19]

Nagata et al.

[11] Patent Number: 4,668,793

[45] Date of Patent: May 26, 1987

[54] PROCESS FOR PRODUCING 1,3-DIMETHYL-2-IMIDAZOLIDINONE

[75] Inventors: Teruyuki Nagata; Nobuyuki Kajimoto; Masaru Wada; Hitoshi Nakayama, all of Fukuoka; Tadao Yamada, Tokyo, all of Japan

[73] Assignee: Mitsui Toatsu Chemicals, Inc., Tokyo, Japan

[21] Appl. No.: 794,034

[22] Filed: Nov. 1, 1985

[30] Foreign Application Priority Data

Nov. 1, 1984 [JP] Japan ............................. 59-228859
Jan. 29, 1985 [JP] Japan ............................. 60-13462

[51] Int. Cl.$^4$ ............................................. C07D 233/34
[52] U.S. Cl. ................................................... 548/317
[58] Field of Search ........................................ 548/317

[56] References Cited

FOREIGN PATENT DOCUMENTS 498245 12/1953 Canada ............................... 548/317
5373561 12/1976 Japan ................................. 548/317

OTHER PUBLICATIONS

Puschin et al. Compounds of Phosgene with Hexamethylenetetramine, m-Toluidine and Ethylenediamine.

*Primary Examiner*—Henry R. Jiles
*Assistant Examiner*—J. Richter
*Attorney, Agent, or Firm*—Sughrue, Mion, Zinn, Macpeak & Seas

[57] ABSTRACT

A process for producing 1,3-dimethyl-2-imidazolidinone with a high yield which comprises reacting N,N'-dimethylethylene diamine and/or its hydrochloride with phosgene in the presence of a substantial amount of water and a dehydrochlorinating agent. Particularly, higher yield is attained by carrying out the reaction in water medium while controlling a pH to the range of 3.0 to 10.0 by adding a dehydrochlorinating agent.

7 Claims, No Drawings

PROCESS FOR PRODUCING 1,3-DIMETHYL-2-IMIDAZOLIDINONE

BACKGROUND OF THE INVENTION

This invention relates to a process for the production of 1,3-dimethyl-2-imidazolidinone and particularly, to an inproved process for producing 1,3-dimethyl-2-imidazolidinone by reaction of N,N'-dimethylethylene diamine with phosgene.

1,3-Dimethyl-2-imidazolidinone (herein referred to as DMI) is a useful substance as a polar non-proton solvent, particularly, for high molecular compounds such as polyamides, polyvinyl chloride, polyvinyl alcohol, polystyrene, polyurethane and phenol resins. Also, DMI is dissolved in form of complex salts with many of inorganic salts and used as a solvent for various organic reactions.

For producing DMI there have been provided, for example, a process of reacting ethylene diamine with urea and reducing formalin adduct of the reaction products obtained with thickloroacetic acid, formic acid or the like, or an improved process on the above reduction, for example, by hydrogenating under an acid condition with use of noble metal catalysts.

Also, there is already provided a process for the production of DMI by reacting N,N'-dimethylethylene diamine with phosgene (J. Chem. Soc., 1947, 307), however, the yield is very low, less than 20% and therefore, it can not be satisfied industrially.

Furthermore, there is provided an improved process effecting the reaction in an organic solvent such as toluene in the presence of a dehydrochlorinating agent and catalyst with use of trichloromethylchloroformate instead of phosgene thereby obtaining DMI with the yield of 70% or more (Japanese Patent Kokai Koho 53-73561). This process is a roundabout way of once forming trichloromethylchloroformate which is a dimer of phosgene and decomposing it to phosgene again by a catalyst to react with the diamine for the production of DMI.

Accordingly, if DMI could be obtained with a high yield starting directly from phosgene, it would be a cheaper and advantageous production process in a commercial scale.

SUMMARY OF THE INVENTION

An object of this invention is to provide an improved process for the production of DMI with a high yield starting from N,N'-dimethylethylenediamine and phosgene.

In accordance with this invention there is provided a process for the production of DMI which comprises reacting N,N'-dimethylethylene diamine with phosgene in the presence of a substantial amount of water and a dehydrochlorinating agent.

In a preferred embodiment of this invention the reaction is carried out in the presence of a substantial amount of water while controlling a pH to the range of 3.0 to 10.0 by addition of the dehydrochlorinating agent whereby DMI can be obtained with higher yield.

DETAILED DESCRIPTION OF THE INVENTION

It is known that the reaction using phosgene is carried out substantially in the absence of water and a large amount of phosgene is required because phosgene is easily hydrolyzed in an alkaline aqueous solution.

Surprisingly, according to this invention, it has been found that phosgene to be used is sufficient with 1.1 to 1.5 times the stoichiometrical amount and the yield of DMI is remarkably increased from the conventional value of less than 20% to the high extent of more than 70% in the presence of a substantial amount of water and a dehydrochlorinating agent.

In accordance with this invention, the production of DMI starting from N,N'-dimethylethylene diamine and phosgene can be performed in uniform state without depositing the resulting N,N'-dimethylethylene diamine hydrochloride outside the reaction vessel and therefore, the controlling of pH can be easily effected during the reaction.

Though the reason why DMI is obtained with the high yield of more than 70% according to the process of this invention is not bound by a theoretical explanation, this is explicable on the basis that the combination of a dehydrochlorinating agent with water acts conveniently to catch hydrochloric acid by-produced in the forming of carbamoylchloride and in the ring-closure reaction of the carbamoylchloride to DMI. If the dehydrochlorinating agent is not used, the starting diamine itself acts as the catching agent for the by-produced hydrochloric acid and therefore, it is difficult to advance further reaction.

Another advantage of this invention is that cheap water can be used as a solvent, that is, since the starting diamine is soluble in water and also, many of dehydrochlorinating agents or its formed salts are soluble in water, the reaction is usually carried out substantially under homogeneous solution so that the reaction velocity is fast and the yield is increased.

Further advantage of this invention is that there is little loss of phosgene while carrying out the reaction in an aqueous solution in the presence of a base and the reaction is advanced approximately in equimol amounts.

According to the preferred embodiment of this invention, the reaction is carried out while controlling a pH to the range of 3.0 to 10.0 whereby DMI is obtained with a high yield unexpected over the prior art.

This reason is explicable on the basis that in the production of DMI by ring-closure reaction of monocarboxychloride of N,N'-dimethylethylene diamine with hydrogen atom bonded to another nitrogen in the molecule, the formation of by-products caused by intermolecular reactions and of N,N'-dicarboxychloride caused by reaction with phosgene can be restrained by the controlling of pH.

In the process of this invention, N,N'-dimethylethylene diamine or its hydrochloride or a mixture thereof is used as the starting material. When the reaction is carried out while controlling the pH to the range of 3.0 to 10.0, N,N'-dimethylethylene diamine is conveniently charged in the form of hydrochloride from the beginning of reaction. In case of N,N'-dimethylethylene diamine dihydrochloride (equivalent of hydrochloride acid) being charged, a pH at the beginning of reaction is about 3.0 and the reaction of the dihydrochloride with phosgene is slow. Accordingly, it is preferred that monohydrochloride which is a reaction product with hydrochloride acid of equivalent or less is used as the hydrochloride. In case of charging dihydrochloride from the beginning it is preferred that dehydrochlorination is preliminarily conducted by a dehydrochlorinating agent to make the pH more than 3.0 and then, the reaction with phosgene is carried out.

Also, when N,N'-dimethylethylene diamine itself is charged to react with phosgene, the pH at the beginning of reaction is 11 or more and therefore, it is advisable that hydrochloric acid is preliminarily added prior to the reaction to make the pH 10 or less.

Water used in this invention may be preliminarily added into a reaction vessel or charged dropwise together with a dehydrochlorinating agent, e.g. in the form of an aqueous solution of alkali metal compounds. Though the amount of water used is not particularly limited, it is preferred to be so sufficient that the homogeneous reaction can be maintained. Concretely, the amount of water is preferably, 0.5~50 parts by weight to 1 part of N,N'-dimethylethylene diamine, more preferably, 5~30 parts by weight.

Also, water may be used together with an organic solvent inert for phosgene, the diamine and DMI. However, in the light of volume efficiency of the reaction vessel and of some formation of by-products, only water is conveniently used in many cases.

The dehydrochlorinating agents used in this invention are, for example, a tertiary amine, e.g. an aliphatic tertiary amine such as trimethylamine and triethylamine, an aromatic tertiary amine such as dimethyl aniline and diethylaniline, a heterocyclic tertiary amine such as pyridine and pyrazine or an alkali metal basic compound such as sodium hydroxide, potassium hydroxide, sodium carbonate and potassium carbonate.

The reaction temperature is not particularly limited, though temperatures of 0° to 70° C. are preferred.

In the preferred embodiment of this invention a pH during reaction is controlled to the range of 3.0 to 10.0, preferably 4.0 to 9.0, more preferably 5.0 to 8.0 by addition of the dehydrochlorinating agent. If the pH is less than 3.0, the selectivity to DMI is high but the reaction velocity has a tendency to decrease, while in case of more than 10.0 the reaction velocity is increased but the selectivity to DMI has a tendency to decrease.

DMI with a remarkably high yield of more than 90% as compared with conventional processes is obtained by controlling a pH to 3.0-10.0. Further strictly controlling the pH, it would be possible to produce DMI with the selectivity of approximately 100%.

The amount of each of phosgene and the dehydrochlorinating agent is not particularly limited, though it is sufficient with 1.1 to 1.5 times the stoichiometrical amount to the starting diamine. Also the amount of the dehydrochlorinating agent to phosgene is sufficient to be approximately stoichiometrical.

A preferred process of embodiment of this invention is carried out as follows:

To a reactor provided with a reflux condenser, a thermometer, a phosgene blowing tube, a dropping funnel, a pH measuring electrode and a stirrer are added water and N,N'-dimethylethylene diamine. Reaction is initiated. Preferably, the pH of the diamine solution is made about 3-10 by addition of hydrochloric acid. The solution is stirred at an appropriate temperature and phosgene is fed through the phosgene blowing tube simultaneously with adding of a dehydrochlorinating agent from the dropping funnel thereby maintaining the pH of the reaction solution at 3.0-10.0.

After completion of the blowing and adding, unreacted phosgene is purged by nitrogen gas and DMI is obtained in conventional methods such as extraction and/or distillation.

This invention will be further illustrated by the following non-limitative Examples.

EXAMPLE 1

To a four-necked, 300 ml flask provided with a reflux condenser, a thermometer, a dropping funnel, a phosgene inlet tube and a stirrer were fed 100 ml of water and 8.8 g (0.1 mol) of N,N'-dimethylethylene diamine and 20.2 g (0.2 mols) of triethylamine was placed in the dropping funnel. The flask was maintained at 20° C. and phosgene was blown off under stirring through the phosgene inlet tube at a blowing rate of 10 g/hr over one hour. Simultaneously, triethylamine was added dropwise from the dropping funnel over one hour. After completion of the blowing and dropping, the reaction mixture was aged at 20° C. for one hour, from which samples were taken out and the determination by gas chromatography of DMI was effected. Theoretical yield of DMI: 75.1%.

COMPARATIVE EXAMPLE 1

To a four-necked, 300 ml flask provided with a reflux condenser, a thermometer, a phosgene inlet tube and a stirrer were added 100 ml of toluene and 8.8 g (0.1 mol) of N,N'-dimethylethylene diamine. The flask was maintained at 20° C. and phosgene was blown off under stirring through the phosgene inlet tube at a blowing rate of 10 g/hr over one hour. After completion of the blowing, the reaction mixture was aged at the same temperature for one hour, from which samples were taken out and the gas chromatography analysis was effected for DMI determination. The theoretical yield of DMI, was only 19.2%.

EXAMPLE 2

The procedure of Example 1 was repeated except using 212 g (0.2 mols) of a 10% aqueous solution of sodium carbonate instead of triethylamine. The theoretical yield by the gas chromatography analysis was 70.8%.

EXAMPLE 3

The procedure of Example 1 was repeated except using 80 g (0.2 mols) of a 10% aqueous solution of sodium hydroxide instead of triethylamine. The theoretical yield by the gas chromatography analysis was 81.3%.

EXAMPLE 4

To a four-necked, 500 ml flask provided with a reflux condenser, a thermometer, a dropping funnel, a phosgene inlet tube, a pH measuring electrode, and a stirrer were fed 100 ml of water, 17.6 g (0.2 mol) of N,N'-dimethylethylene diamine and 30.4 g (0.3 mols) of a 36% hydrochloric acid. The pH of the diamine solution was 7.3. On the other hand 168.0 g (0.8 mols) of a 20% aqueous solution of sodium hydroxide were placed in the dropping funnel. The reaction temperature was maintained to 20° C. under cooling and phosgene was blown off under stirring at a rate of 10 g/hr over two hours. Simultaneously, the aqueous solution of sodium hydroxide was added dropwise over two hours thereby controlling the pH to 7.3±0.2.

After completion of the blowing and adding, the reaction apparatus was purged by nitrogen gas of 20 l/min. over 0.2 hours. The reaction mass was sampled for the gas chromatography analysis and as a result, 0.8 g (conversion ratio, 95.4%) of unreacted N,N'-dimethylethylene diamine and 21.2 g (selectivity, 97.5%) of DMI were obtained.

To the solution after completion of reaction was added a 48% aqueous solution of sodium hydroxide thereby making the pH 10 and thereafter, extraction with 150 g of 1,2-dichloroethane was twice conducted and the 1,2-dichloroethane layer was separated followed by distillation. The initial fraction included 0.6 g of N,N'-dimethylethylene diamine and the main fraction included 20.3 g of DMI (theoretical yield 92.1%). The purity of this main fraction DMI was 99.5%.

EXAMPLE 5

To the same reactor as in Example 4 were fed 40.6 g (0.4 mols) of a 36% hydrochloric acid in the same manner as in Example 4. The diamine solution had the pH of 3.0. While controlling the pH during the reaction to 4.8±0.3, the reaction was carried out in the same conditions as in Example 4. As a result of analysis, 7.0 g (conversion, 60.2%) of unreacted N,N'-dimethylethylene diamine and 13.6 g (selectivity, 99.0%) of DMI were formed.

EXAMPLE 6

To the same reactor as in Example 4 were added 20.2 g (0.2 mols) of a 36% hydrochloric acid in the same manner as in Example 4. The diamine solution has the pH of 9.0. While controlling the pH during the reaction to 9.0±0.3, the reaction was carried out in the same conditions as in Example 4. As a result of analysis, 1.7 g (conversion, 90.3%) of unreacted N,N'-dimethylethylene diamine and 18.7 g (selectivity, 90.7%) of DMI were formed.

COMPARATIVE EXAMPLE 2

The materials were fed to the reactor in the same conditions as in Example 4 except not using a 36% hydrochloric acid. The pH of the diamine solution was 11.5. While controlling the pH during the reaction to 10.5±0.2, the reaction was carried out in the same conditions as in Example 4. As a result of analysis 0.2 g (conversion, 98.8%) of unreacted N,N'-dimethylethylene diamine and 18.0 g (selectivity, 79.8% were formed.

What is claimed is:

1. A process for the production of 1,3-dimethyl-2-imidazolidinone which comprises reacting N,N'-dimethylethylene diamine with phosgene in the presence of a substantial amount of water and a dehydrochlorinating agent.

2. A process for the production of 1,3-dimethyl-2-imidazolidinone which comprises reacting N,N'-dimethylethylene diamine, N',N'dimethylene diamine hydrochloride salt or mixtures thereof with phosgene in a water medium while controlling the pH to the range of 3.0 to 10.0 by adding a dehydrochlorinating agent.

3. A process of claims 1 or 2 wherein the amount of water is within the range of 0.5 to 50 times by weight the amount of N,N'-dimethylethylene diamine.

4. A process of claims 1 or 2 wherein the amount of phosgene is in the range of 1.1 to 1.5 times the stoichiometrical amount to the starting diamine.

5. A process of claim 2 wherein the reaction is carried out at a pH of 4.0 to 9.0.

6. A process of claims 1 or 2 wherein said dehydrochlorinating agent is selected from an aliphatic, aromatic and heterocyclic tertiary amine.

7. A process of claims 1 or 2 wherein said dehydrochlorinating agent is selected from alkali metal basic compounds.

* * * * *